Figure 1:
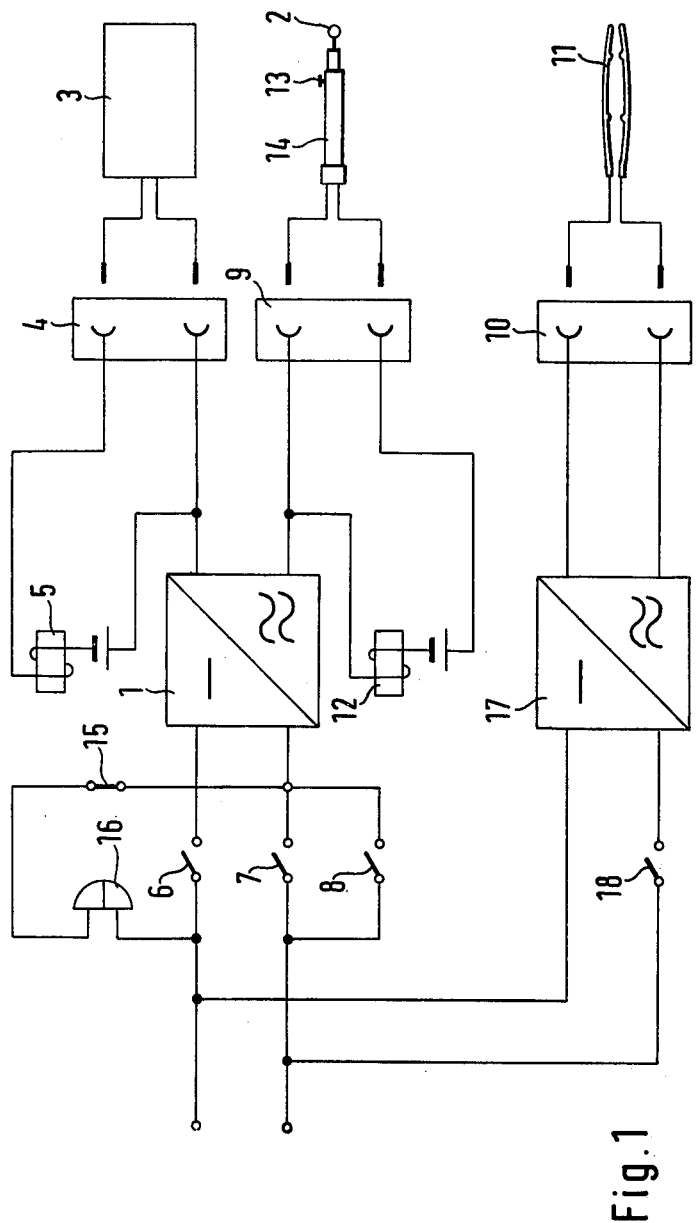

United States Patent [19]

Farin

[11] 4,171,700
[45] Oct. 23, 1979

[54] HIGH-FREQUENCY SURGICAL APPARATUS

[75] Inventor: Günter Farin, Tübingen-Hirschau, Fed. Rep. of Germany

[73] Assignee: Erbe Elektromedizin GmbH & Co. KG, Tübingen, Fed. Rep. of Germany

[21] Appl. No.: 841,983

[22] Filed: Oct. 13, 1977

[30] Foreign Application Priority Data

Oct. 13, 1976 [DE] Fed. Rep. of Germany ....... 2646228
Oct. 13, 1976 [DE] Fed. Rep. of Germany ....... 2646229

[51] Int. Cl.$^2$ .................... A61B 17/36; A61N 3/02
[52] U.S. Cl. ....................... 128/303.14; 128/303.17
[58] Field of Search ................ 128/303.13, 303.14, 128/303.15, 303.17, 303.18

[56] References Cited

U.S. PATENT DOCUMENTS

| 3,683,923 | 8/1972 | Anderson | 128/303.14 |
| 4,051,855 | 10/1977 | Schneiderman | 128/303.14 |

FOREIGN PATENT DOCUMENTS

| 2044078 | 5/1972 | Fed. Rep. of Germany | 128/303.14 |
| 2150586 | 4/1973 | France | 128/303.14 |

*Primary Examiner*—Lee S. Cohen
*Attorney, Agent, or Firm*—Frishauf, Holtz, Goodman & Woodward

[57] ABSTRACT

In a high-frequency surgical apparatus having a number of electrode-connections for a neutral electrode and a number of electrodes, respectively, for monopolar and bipolar operation, two high-frequency generators are connected to a single voltage source, so that the second generator may serve exclusively for supplying a high-frequency current to the electrode-connections for bipolar electrodes. A warning signal is produced only if a switch is closed for a monopolar use, even if the neutral electrode is not properly connected. Therefore the bipolar high-frequency generator may be actuated independently of whether a natural electrode is connected to the apparatus or not. In this manner unintended injuries or damages by a contact with an electrode are avoided. In an alternate embodiment of the invention only a single high-frequency generator is provided in combination with a switch-over device for switching over between bipolar and monopolar use, so that in the case of bipolar use the protective circuit is disabled. Examples for the field of use of such electrosurgery units are Dermatology, Gynaecology, Opthalmology, Dental Surgery, ENT and Cosmetic Surgery.

1 Claim, 2 Drawing Figures

HIGH-FREQUENCY SURGICAL APPARATUS

The present invention relates to a high-frequency surgical apparatus e.g. for use in producing coagulation of body tissues in high-frequency electric surgery. Such surgical apparatus is normally provided with a neutral electrode and activatable electrodes for monopolar and for bipolar operation, and is provided with a protective circuit, which in the case of an interruption of the electrical connection between the neutral electrode and its connection at the apparatus also interrupts the supply of energy from the high-frequency generator to the active electrode or electrodes and indicates the interruption by an alarm signal.

In the case of known high-frequency surgical apparatus of this type, which are provided with electrode contacts for a monopolar as well as for a bipolar use, the high-frequency current for the monopolar as well as for the bipolar use is supplied from a single high-frequency generator. Though it is possible in the case of such known surgical apparatus, to adjust the output power for the monopolar use and the bipolar use, respectively, independently from each other at the apparatus, still a number of problems are involved in the practical use of such apparatus.

During the activation of the high-frequency generator high-frequency electrical voltage is present simultaneously on all connections, this voltage being aplied to the connections of both the monopolar and the bipolar electrodes. If monopolar and bipolar electrodes are simultaneously connected with the surgical apparatus, the danger exists, that the excited but unused electrode may cause damage to materials and devices or even injure the patient or attending personnel. In the case of a monopolar use of such surgical apparatus with higher output power it is necessary, furthermore, to provide a protective circuit, which in the case of a break of the electrically conducting connections between the neutral electrode and its contact at the apparatus also interrupts the supply of energy to the active electrode and indicates the interruption by an alarm signal. Therefore, it is also necessary in the case of a bipolar use, in which a neutral electrode is not needed, to connect a neutral electrode, since otherwise the protective circuit of the neutral electrode, which is provided for safety reasons, would hinder the activation of the high-frequency generator. Furthermore, there is no risk of injury especially in the case of high-frequency surgical apparatus in which the neutral electrode has a "floating" output, i.e., where the neutral electrode and therewith also the patient connected to the neutral electrode are at a high-frequency potential relative to ground potential. This voltage has its maximum value if the active output of the monopolar circuit is short-circuited to the ground potential. Accidental injury is possible if the active electrodes are brought in contact with a grounded object intentionally. In such apparatus always the danger exists, that high-frequency current will flow from the neutral electrode into the bipolar electrode and return through practically unavoidable leakage capacitance to the high-frequency generator. Such currents should be avoided in the bipolar mode of operation.

It is therefore the primary object of the present invention to provide a high-frequency surgical apparatus which avoids problems of the above-mentioned type so that on the one hand the operating reliability (safety) can be improved and on the other hand the control, operation and use of the apparatus is simplified.

SUMMARY OF THE INVENTION

Briefly, in parallel to a first high-frequency generator a second high-frequency generator is connected through a switch to the supply voltage source of the first high-frequency generator. The switch provides for putting the second high-frequency generator into operation connectable independently of the first high-frequency generator. This second high-frequency generator is provided exclusively for supplying of high-frequency current to the electrode connections for bipolar electrodes connected therewith.

Therefore, in such a high-frequency surgical apparatus the high-frequency generator for the monopolar use is provided in a conventional manner with a protective circuit for the neutral electrode. However, a warning signal is caused in the case of a failure with respect to the continuity of the electrical connection between the high-frequency surgical apparatus and the neutral electrode only if a foot-switch or a finger-switch for the monopolar use is inactivated position. In this manner, confusion is avoided from the warning signal always appearing if the neutral electrode is not connected, while the the high-frequency surgical apparatus is connected to the power mains. Such false warnings are particularly disturbing if only bipolar operation as being performed, in which case the neutral electrode is not necessary. The bipolar high-frequency generator may be operated independently of whether a neutral electrode is connected with the surgical apparatus or not. In other words, if the neutral electrode is not connected to the high-frequency surgical apparatus, operation in the bipolar mode is not prevented by the protective circuit of the neutral electrode.

In a second embodiment of the invention only a a single high-frequency generator is provided and a switch-over means for switching over between bipolar and monopolar use is provided, so that in the case of the bipolar use the protective circuit is switched off.

Preferably the switch-over means contains switches coupled with each other and connected in such a manner between the output of the high-frequency generator and the electrode connections, that in the one switch position only the electrode connections for bipolar electrodes are connected with the high-frequency generator so that one of the switches then disconnects the protective circuit. In the other switching position only the electrode connections for the neutral electrode and the electrode connections for the monopolar electrode are connected, and the mentioned switch connects the alarm device with the protective circuit. Therefore, in the case of bipolar use the high-frequency generator will also be then activated, if the neutral electrode is not connected to the high-frequency surgical apparatus, whilst in the case of monopolar use the activation of the high-frequency generator is only possible, if the neutral electrode is properly connected with the high-frequency surgical apparatus.

Figure 2:
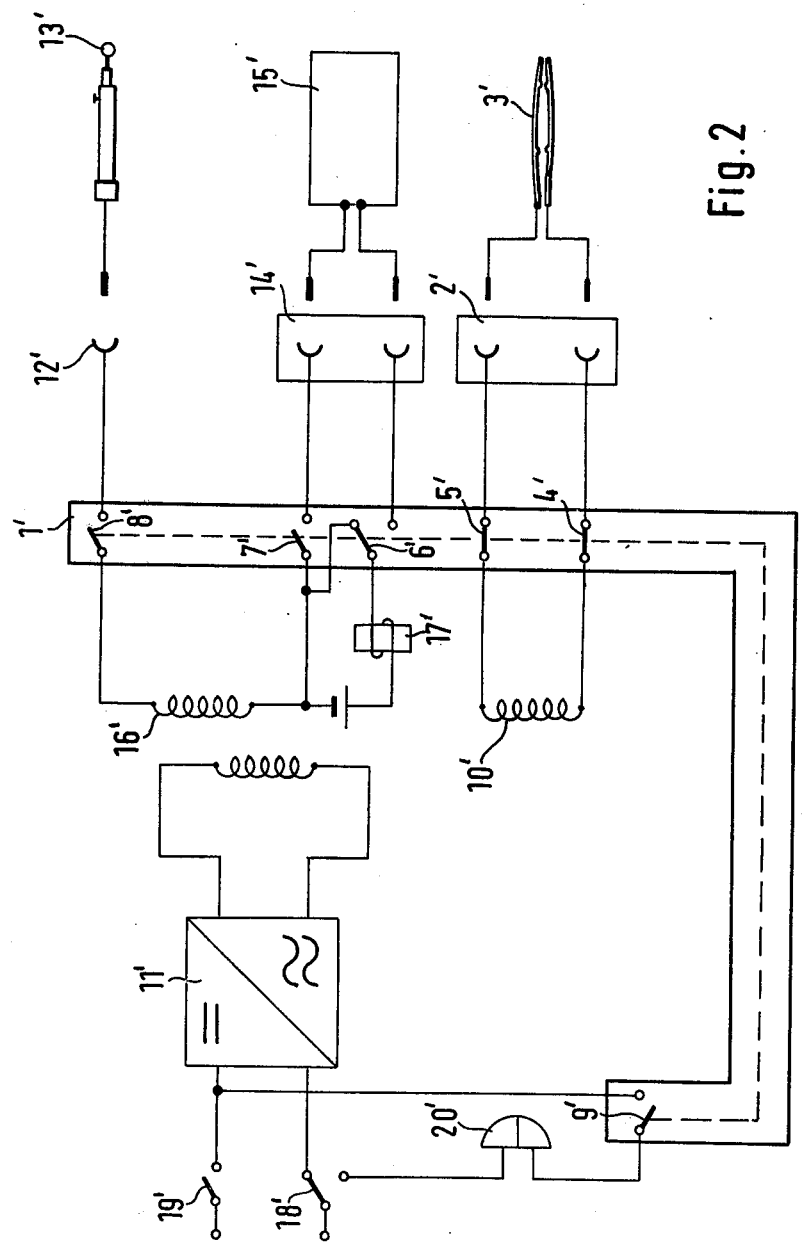

The invention is further described by way of specific examples with reference to the annexed drawings, in which:

FIG. 1 is a schematic circuit diagram of a high-frequency surgical apparatus in accordance with the invention containing two high-frequency generators, and FIG. 2 a circuit diagram of an alternate embodiment of a high-frequency surgical apparatus in accordance with the invention, containing a single high-frequency generator and a switch-over means.

In the case of the first embodiment of a high-frequency surgical apparatus as shown in FIG. 1 two high-frequency generators 1, 17 are provided independently from each other. The one high-frequency generator 1 produces the high-frequency current for a monopolar active electrode 2, having a handle 14 provided with a finger-switch 13. This electrode is connected through an electrode-connection 9 with the high-frequency generator 1. This high-frequency generator 1 can only be switched on, if a neutral electrode 3 necessary for a monopolar use is properly connected to electrode connections 4, in which case circuit for exciting a relay 5 is closed and a switch 6 operated thereby connects the supply of current for the high-frequency generator 1. Upon closing of a foot-switch 7 the high-frequency generator 1 produces high-frequency current which is supplied only to the electrode-connections 4 of the neutral electrode and the electrode-connections 9 of the monopolar active electrode 2. In this situation no current is supplied to the electrode-connections 10 for the bipolar electrode 11 these being connected to the now inactive second high-frequency generator 17.

Instead of the foot-switch 7 a relay-switch 8 may be closed by means of a relay 12, if the push button 13 at the handle 14 is pressed down by the surgeon's finger. During the connection of the neutral electrode with the electrode-connections 4 a relay-switch 15 is opened by the relay 5, so that an alarm device 16 will not produce an alarm signal if one of the switches 7, 8 is closed. However, if the neutral electrode 3 is not properly connected with the electrode-connections 4, then the relay-switch 15 is not opened by the relay and the alarm device 16 supplies a warning signal as soon as one of the switches 7 or 8 is closed.

The high-frequency generator 17 may be switched on through a foot-switch or a finger actuated switch 18 independently of whether or not the neutral electrode 3 is connected with the electrode-connections 4. If it is desirable to prevent the two high-frequency generators 1, 17 from being switched on simultaneously, a switch-over means may be provided in the mains-connecting circuit of the two high-frequency generators, instead of providing the switch 18, so by closing of the one of the switches 7 or 8 the particular generator selected beforehand by the switchover means will be connected with its power supply subject of course to the protective circuit in case of the generator 1. Preferably, the electrode-connections 4, 9 and 10 may be designed in such the proper manner, that only a electrode may be connected with electrode-connections provided for this specific electrode.

In the embodiment of the invention in FIG. 2 a switch-over means is provided, comprising switches 4' to 9' coupled with each other. In the shown switching position only the electrode-connections 2' for a bipolar electrode 3' are connected to the single high-frequency generator 11' through its first secondary coil 10'. In the other position of the of the switches the electrode connections 14' for a neutral electrode 15' and an electrode-connection 12' for a monopolar electrode 13' are connected through the second secondary coil 16' of the high-frequency generator 11'. In the protective circuit, which in the case of an interruption of the electrically conducting connection between the neutral electrode and its connection at the apparatus also interrupts the energy supply to the active monopolar electrode 13' and actuates an alarm device 20', a relay 17', is provided which upon switching-over to bipolar use actuates a switch 18', if the energizing circuit for the relay is closed.

Now the operation will be discussed in more detail. In the position of the switches 4' to 9' as shown in FIG. 2 bipolar operation takes place, while the electrode-connections 12' for the monopolar electrode 13' and the electrode-connections 14' for the neutral electrode 15' are separated from the secondary circuit 16' of the high-frequency generator 11'. Since then switch 6' closes the energizing circuit for the relay 17', in the shown position of the switch 18' the current supply for the high-frequency generator 11' is prepared. If then a finger- or foot-switch 19' is closed, the high-frequency generator 11' is switched on and high-frequency current may be drawn from the electrode-connections 2', while no voltage is supplied to the electrode-connections 12' and 14'. Regardless of whether the neutral electrode 15' is connected with the electrode-connection 14' or not, the alarm device 20' is then unable to produce an alarm signal.

If the switching-over means 1' is switched over to monopolar use, the switches 6' and 7' connect the neutral electrode 15' through the electrode-connections 14'. If the neutral electrode 15' is connected with the electrode-connections 14', the energizing circuit for the relay 17' is dosed and the switch 18' in the shown position connects the current supply to the high-frequency generator 11'. Upon closing of the finger- or foot-switch 19' the high-frequency generator 11' may then be switched on. The electrode-connections 12' and 14' are then supplied with the high-frequency current through the switches 8' and 7' from the secondary coil 16' of the high-frequency generator, while the electrode-connections 2' are not under voltage, since the switches 4' and 5' are opened. Upon separating the neutral electrode 15' in the position of the switches for monopolar use from the electrode-connection 14', the operating circuit for the relay 17' is interrupted and the switch 18' deenergizes the high-frequency generator 11', so that the operating circuit of the alarm device 20' is closed by the switches 18' and 9' and an alarm signal is provided.

Although the invention has been described with reference to particular illustrative embodiments, it is evident that variations may be made within the inventive concept.

We claim:
1. High-frequency electrical surgical apparatus for use with manipulable electrodes through electrode-connections of the apparatus and having electrode-connections respectively, for a neutral electrode, at least one electrode for monopolar operation, and at least two electrodes for bipolar operation, the apparatus having a first high-frequency generator, an electric power source connected to the input circuit of the first high-frequency generator for powering the same and being provided with protective circuit means responsive to interruption of the electrically conducting connection between the neutral electrode and its connection at the apparatus for interrupting the energy supply provided by the first high-frequency generator to said at least one electrode and for producing an alarm signal indicative of said first-mentioned interruption, having the improvement which consists in that:

a second high-frequency generator is provided parallel to said first high-frequency generator; a switch connecting the input circuit of the second high-frequency generator with the electric power source of the first high-frequency generator, said second high-frequency generator being connectable independently of the first high-frequency generator to the electric power source by closing of said switch; said second high-frequency generator is exclusively provided, and connected, for supplying of high-frequency current to the electrode-connections for said bipolar electrodes; and said protective circuit means includes means to disable at least its producing of said alarm signal except when said first high-frequency generator is in use.

* * * * *